US006972282B1

(12) United States Patent
Tossavainen et al.

(10) Patent No.: US 6,972,282 B1
(45) Date of Patent: Dec. 6, 2005

(54) PROCESS FOR PRODUCING A PRODUCT CONTAINING ANTIHYPERTENSIVE TRIPEPTIDES

(75) Inventors: Olli Tossavainen, Espoo (FI); Tarja Suomalainen, Helsinki (FI); Janne Sahlstein, Helsinki (FI); Annika Mäyrä-Mäkinen, Helsinki (FI)

(73) Assignee: Valio Ltd., Helsinki (FI)

( * ) Notice: Subject to any disclaimer, the term of this patent is extended or adjusted under 35 U.S.C. 154(b) by 255 days.

(21) Appl. No.: 10/111,942

(22) PCT Filed: Oct. 30, 2000

(86) PCT No.: PCT/FI00/00942

§ 371 (c)(1),
(2), (4) Date: May 7, 2002

(87) PCT Pub. No.: WO01/32905

PCT Pub. Date: May 10, 2001

(30) Foreign Application Priority Data

Nov. 1, 1999 (FI) ................................. 19992360

(51) Int. Cl.[7] ..................... A61K 38/00; C12P 21/06; A23C 9/12; B01D 39/14
(52) U.S. Cl. ..................... 514/18; 435/68.1; 435/252; 210/652; 426/43
(58) Field of Search ....................... 514/18; 435/168.1, 435/252, 68.1; 210/652; 426/41, 43

(56) References Cited

U.S. PATENT DOCUMENTS

| 4,409,247 A | * | 10/1983 | Baret et al. ................... 426/41 |
| 5,449,661 A | | 9/1995 | Nakamura et al. |
| 6,514,941 B1 | * | 2/2003 | Tolton et al. .................. 514/14 |

FOREIGN PATENT DOCUMENTS

| EP | 0 737 690 A2 | 10/1996 |
| EP | 0 821 968 A3 | 7/1999 |
| FI | 104783 B | 4/2000 |
| GB | 2 294 191 A | 4/1996 |
| JP | 11-98978 | * 4/1999 |
| WO | 99/16862 | 4/1999 |

OTHER PUBLICATIONS

Jeantet et al. "Semicontinuous production of lactic acid in a bioreactor coupled with anofiltration membranes" Enz. Microb. Technol. (1996) 19: 614-619.*
Webster's II New Riverside Dictionary (1994) (Houghton-Mifflin: Boston MA) p. 417.*
WPI, Derwent, accession No. 1986-110323, Calpis Shokuhin Kogyo KK: "Drug for prophylaxis of hypotension—contains high mol. substance obtd. by removing cell and casein from fermented milk", & JP 61053216, 19860317.
PAJ/JPO, "Peptide, Angiotensinase Inhibiting Composition and Their Production", Otsuka Shokuhin KK, &JP 9188694, 19970722'.
Anne Pihlanto-Leppala et al; "Angiotensin I Converting Enzyme Inhibitory Peptides Derived from Bovine Milk Proteins", Int. Dairy Journal, vol. 8, 1998, p. 331.
Jeantet, R. et al; Caplus Copyright 2001 ACS, accession No. 1996:467944, "*Nanofiltration* benefit for production of spray-dried demineralized whey powder", 1996, vol. 76 (3), pp. 283-301.
Hutosn, T.; "* Nanofiltration* and ion exchange for the demineralization of whey",Int. Dairy Fed, 1998, vol. 9804, pp. 88-92, ISSN: 1025-8515.
Bouhallab et al; accession No. 1995:899699 Caplus, "Continuous hydrolysis of caseinomacropeptide in a membrane reactor: Kinetic study and gram-scale production of antithrombotic *peptides*", 1995, vol. 75(3), pp. 251-258.
Yamamoto Naoyuki et al; "Antihypertensive Effect of the Peptides Derived From Casein by an Extracellular Proteinase from Lactobacillus Helvetlcus CP790", J Dairy Sci., vol. 77, 1994, pp. 917-922.
WPI, Derwent, accession No. 1994-268691, Calpis Shokuhin Kogyo KK: "Prepn. of peptide whichinhibits angiotensin conversion enzyme-by lactic acid bacterium culture of material with specified tri: peptide sequence"; & JP A 6197786, 19940719.
Yasunori, Nakamura et al.; "Purification and Characterization of Angiotensin I-Converting Enzyme Inhibitors from Sour Milk", J. Dairy Sci., 1995, vol. 78, pp. 777-783.
Yamamoto et al J. Biochem 114, 740-745 (1993) Purification and Specificity of a Cell-Wall-Associated Proteinase from *Lactobacillus helveticus* CP790.
Holmquist et al Analytical Biochemistry 95, 540-548 (1979) A continuous Spectrophotometric Assay for Angiotensin Converting Enzyme.

* cited by examiner

Primary Examiner—Jean C. Witz
Assistant Examiner—Susan Hanley
(74) Attorney, Agent, or Firm—Nixon & Vanderhye P.C.

(57) ABSTRACT

The invention relates to a process for preparing a product containing antihypertensive peptides by fermenting a casein-containing starting material with lactic acid bacteria. The invention also relates to the obtained product and its use as a functional product as such or as an ingredient or additive of edible substances.

24 Claims, 1 Drawing Sheet

PROCESS FOR PRODUCING A PRODUCT CONTAINING ANTIHYPERTENSIVE TRIPEPTIDES

This application is the US national phase of international application PCT/FI00/0942 filed 30 Oct. 2002, which designated the US.

FIELD OF THE INVENTION

The invention relates to a process for preparing a product containing antihypertensive peptides. The invention also relates to the obtained product and its use as a functional product as such or as an ingredient or additive in edible substances.

BACKGROUND OF THE INVENTION

At present, cardiovascular diseases are counted among the most common national diseases in developed countries and their occurrence will further increase as the population grows older. High blood pressure contributes considerably to the development of these diseases. Therefore, treating hypertension is one of the most important measures regarding both prevention and effective treatment.

In blood pressure control, an angiotensin-I-converting enzyme, ACE, has a key role on a cell level. ACE functions in two ways: it converts angiotensin I to angiotensin II which is a strong vasopressor and inactivates bradykinin which, in turn, has a vasodilatory effect. Thus, both functions lead to elevated blood pressure. ACE inhibitors may inhibit this effect and consequently act as antihypertensive agents. Many known pharmaceuticals used in treatment of hypertension are ACE inhibitors. One of these is captopril, i.e. D-2-methyl-3-mercaptopropanoyl-L-proline, which is commercially available in Finland under trade names Capoten (by Bristol-Myers Squibb) and Captopril Generics (by Merck Generics).

Other methods to lower high blood pressure have also been sought as an alternative to medication, or in addition thereto. These include, for instance, to avoid obesity, to increase exercise and to consume a low-sodium diet. One of the newest ways is to use functional foods as a part of a normal diet, which the consumers have found to be a welcome alternative.

Fermented milk products have been reported to contain peptides having an antihypertensive effect. It is assumed that the peptides are produced in the milk products as a result of milk protein hydrolysis effected by lactic acid bacteria and particularly extracellular proteinases thereof. In *J. Biochem.* 114 (1993) 740, Yamamoto et al. describe purification and characterisation of a proteinase derived from the microorganism *Lactobacillus helveticus* CP790. Yamamoto et al. have also reported on a study in which $\alpha_{s1}$- and $\beta$-casein were hydrolysed with said proteinase and the obtained peptides were studied for their ACE-inhibitory effect (*J Dairy Sci* 77 (1994) 917). The studied peptides were 25 in total, and their molecular sizes and effects were greatly different. The most active ones were three peptides obtained from $\beta$-casein and containing 8, 18 and 27 amino acids respectively. The study also compared ACE-activity of milk fermented with the strain *Lactobacillus helveticus* CP790 and its variant CP791 with defective proteinase activity, whereby the former was found effective in spontaneously hypertensive SHR rats but not in an ordinary rat strain, whereas the latter had no activity at all.

In *J Dairy Sci* 78 (1995) 777–783, Nakamura et al. describe the use of a starter containing *Lactobacillus helveticus* and *Saccharomyces cerevisiae* for the preparation of two ACE inhibitors. Fat-free milk was fermented with said starter, whereafter the ACE inhibitors were purified chromatographically and analyzed. The active compounds were both tripeptides, Val-Pro-Pro and Ile-Pro-Pro. The publication does not describe an in vivo antihypertensive effect of the tripeptides and the sour milk product prepared with the starter, but it is mentioned to be the next subject of research.

U.S. Pat. No. 5,449,661 (Nakamura et al.) discloses the preparation of a peptide containing the tripeptide sequence Val-Pro-Pro and its use for lowering high blood pressure. The peptide is prepared by fermenting fat-free milk powder with the *Lactobacillus helveticus* strain JCM-1004, whereafter the peptide is purified chromatographically and freeze-dried.

International Patent Application WO99/16862 (Yamamoto et al) describes the *Lactobacillus helveticus* strain CM4, FERM BP-6060, which is capable of producing a large amount of the tripeptide Val-Pro-Pro and/or Ile-Pro-Pro and which exhibits a high extracellular protease activity. The publication also describes fermented milk products containing said tripeptides and bacterium, and a method for preparing them by fermenting products containing the tripeptide sequences with said bacterium.

Two disadvantages are associated with the products containing antihypertensive peptides prepared by fermentation reactions of lactic acid bacteria. The main product of fermentation is lactic acid, and it is produced the more the more effective the fermentation reaction. As appears from the term itself, lactic acid is acidic and gives a bitter taste to the product containing antihypertensive peptides, in addition to which many consumers find the high acidity and low pH unpleasant. A large number of monovalent ions, particularly sodium ions, are also present in the product containing antihypertensive peptides prepared by fermentation. These ions are known to elevate blood pressure, and hence they act in the opposite direction from the desired, antihypertensive peptides.

Prior art discloses methods of purifying peptides produced in fermentation. These methods allow to partly avoid the above disadvantages, while a concentrated product is obtained. However, the object of the prior art methods has been to provide pure products that are suitable for analyses and activity tests. Hence, the methods are multi-step methods that mainly consist of various chromatographic purifications and that are not suitable for large-scale production.

Therefore, there is still an obvious need to provide new functional products which have an antihypertensive effect and which the consumers find pleasant and familiar, and which therefore can be readily used as a part of the normal diet. It is important that the products do not contain unpleasant or even harmful components and that they are easy to produce on an industrial scale.

SUMMARY OF THE INVENTION

The object of the present invention is thus to provide a product having a high content of antihypertensive peptides and consequently having an antihypertensive effect.

Advantageously, in addition to the high content of antihypertensive peptides, the product of the invention has an advantageous salt content, which means that the amount of harmful monovalent cations is low and the amount of beneficial divalent cations is high as compared with a known product of similar type.

The object of the present invention is also to provide a process for preparing such a product, which process is simple and easy to carry out and therefore suitable for manufacturing the product on an industrial scale.

Further, the object of the present invention is to provide the product for use as such as an antihypertensive agent or in the manufacture of edible functional foods or pharmaceuticals.

In addition, the object of the present invention is to provide for use orally ingested products, such as functional foods and pharmaceuticals, which contain the above-described product as one of the active ingredients.

DETAILED DESCRIPTION OF THE INVENTION

Figure 1:
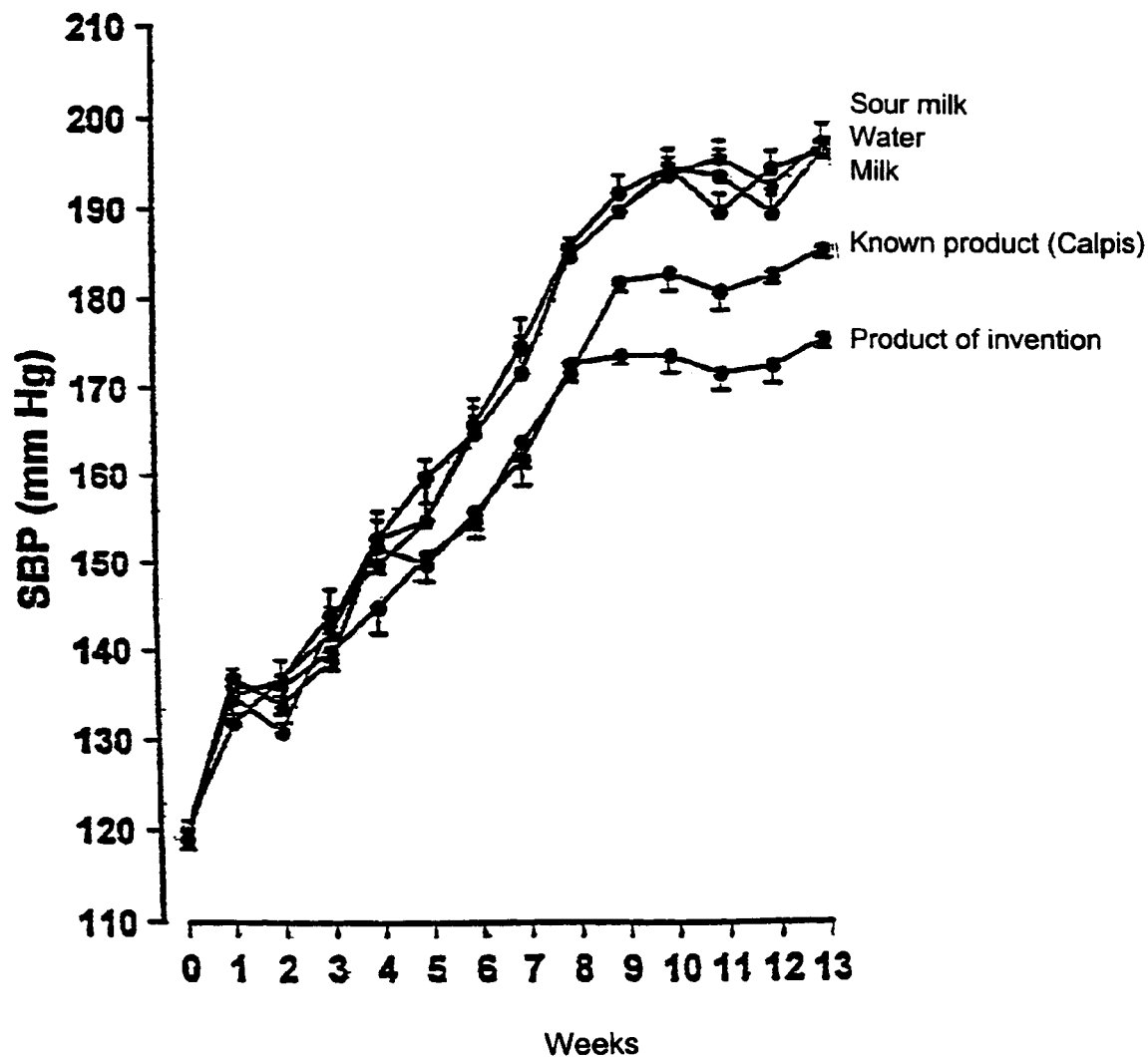
FIG. 1 shows the rise in the systolic pressure as a function of time.

According to the present invention, it has been found that these objects can be achieved with a new process which is based on a new and inventive combination: a pre-preparation containing antihypertensive peptides is produced by fermentation, whereafter it is concentrated and the composition is finalized by nanofiltration. The combination according to the invention provides excellent possibilities to use starting materials of different types and to modify the composition of the end product to be of the desired type, as will be described in greater detail in the following.

Thus, the invention relates to a process for preparing a product containing antihypertensive peptides, the process being characterized by comprising the steps of fermenting a casein-containing starting material with a lactic acid bacterium and performing nanofiltration on the obtained, peptide-containing fermentation product.

The invention also relates to a product containing antihypertensive peptides, which product is characterized by having a high content of antihypertensive peptides and being prepared by a process in which the casein-containing starting material is fermented with a lactic acid bacterium and the obtained peptide-containing fermentation product is nanofiltrated.

The invention also relates to the use of the above-described product as an antihypertensive agent.

The invention further relates to the use of the above-described product in the manufacture of edible substances.

The invention also relates to edible products containing the above-mentioned concentrated product with high peptide content and conventional ingredients of said end products.

In the first step of the process according to the invention, a pre-preparation containing antihypertensive peptides is produced by fermentation. In fermentation, the starting material to be used can be any product which contains sequences of desired antihypertensive peptides as a part of their own peptide or protein sequence. Milk protein, particularly casein, is advantageously used as such or in the form of various preparations. Advantageously, suitable starting materials also include various casein-containing milk products, such as fat-free milk, or milk with varying fat content, as such or in the form of corresponding milk powder, and fermented milk products, such as sour milk, buttermilk, yogurt, curdled milk, unripened cheeses, etc.

Fermentation can be carried out with any lactic acid bacterium that is capable of producing antihypertensive tripeptides from the starting material. Suitable lactic acid bacteria can be found among species of e.g. *Lactobacillus, Lactococcus, Leuconostoc, Streptococcus* and *Bifidobacterium* genera. *Lactobacillus helveticus* is the most proteolytic of the lactic acid bacteria, and therefore it is considered particularly suitable for this purpose. An advantageous *Lactobacillus helveticus* strain is *L. helveticus* LBK-16H. Lactic acid bacteria can be used as pure cultures or mixed cultures, separately or with conventionally used and commercially available starters. Lactic acid bacteria can also be used together with other microorganisms. As regards combinations of microbes, appropriate combinations are selected to the effect that the best possible flavour is achieved in the end product and any contamination risk is avoided.

Fermentation conditions are selected to meet the requirements of the strain to be used in the fermentation such that a sufficient amount of antihypertensive peptides is formed to provide a desired effect. Selection of suitable conditions, such as temperature, pH and aeration, are part of the knowhow of a person skilled in the art. The temperature can be 30 to 45° C., for instance.

Fermentation is allowed to continue until the desired amount of antihypertensive peptides is formed. Normally, this takes about 20 to 30 hours, preferably 22 to 24 hours.

A mixture of various peptides is formed in fermentation. When fermentation takes sufficiently long, relatively small di- and tripeptides, such as Val-Pro-Pro (VPP) and Ile-Pro-Pro (IPP) are mainly obtained.

After fermentation, the cell suspension is recovered. It can be used as such in a next step, i.e. for separating and concentrating peptides. The cell suspension can also be concentrated, for instance, by evaporation or by drying it partly or completely, such as by spreading it onto a plate, drying and finally grinding it to well preservable dry powder.

In some cases, it may be appropriate to subject the fermented product to a pretreatment, for instance, to remove casein or all milk proteins therefrom prior to nanofiltration. The methods applicable to the pretreatment are known in the field and comprise e.g. various precipitation and filtration methods. One useful method comprises adjusting pH of the fermented product to a region where casein precipitates, e.g to 4.6 at a temperature of about 37° C., whereafter the precipitated casein is separated by means of a curd separator, a casein separating sieve, a decanter or by depositing or some other suitable method. A second method comprises ultrafiltration of the fermented product, at a pH of 3 to 3.5, whereby all proteins are retained on the membrane and the obtained permeate is nearly protein-free whey. Coprecipitation which produces nearly protein-free, peptide-containing whey can be achieved, for instance, with addition of $CaCl_2$, heat treatment or addition of acid. When necessary, possible casein dust is removed by centrifugation. Other substances, such as lactose, can also be removed prior to nanofiltration, for instance, by enzymatic hydrolysis or fermentation.

The fermentation product, which has possibly been pretreated in an appropriate manner, such as the whey obtained as described above, is then subjected to nanofiltration. A conventional NF membrane, such as Nanomax-50 (Millipore) or Desal 5 (Desal Inc., USA), can be used as the nanofiltration membrane, and the conditions are selected to meet the requirements and instructions of membrane manufacturers. Selection of the nanofiltration membrane type and process conditions contribute considerably to the composition of the resulting peptide fraction, in particular to the salt and sugar composition.

According to the invention, the nanofiltration is performed to a desired dry matter content or volumetric concentration ratio, which generally is as high as possible. The dry matter content is in the order of about 20 to 40% and the volumetric concentration ratio is about 5 to 20. The (whey) concentrate can be diluted with water, whereby more salts and lactic acid can be removed from the concentrate in nanofiltration. This is a simple and efficient way to adjust the amount of salts in the concentrate to the desired level.

Small peptides, such as the tripeptides IPP and VPP of about 350 D, formed in fermentation and having an effect on blood pressure, are completely retained by means of the nanofiltration membrane. The process of the invention also enables complete removal of lactose: prior to the nanofiltration step, lactose can be enzymatically degraded, whereby the major part of the monosaccharides are removed. In the nanofiltration, included in the process of the invention, lactic acid, small-molecular nitrogen compounds, such as urea, and monovalent salts also permeate the membrane. Hence, the peptide content of the product increases by means of the nanofiltration. Due to concentration, the content of divalent ions, in particular the desired calcium and magnesium ions, increase, whereas the relative proportion of monovalent ions, such as sodium, potassium and chloride ions, decreases. Particularly sodium ions are known to have a considerable effect on the fluid balance and blood pressure in the human body, and therefore a decrease in the amount of these harmful ions can be regarded as a very considerable advantage. Calcium and magnesium ions, in turn, are known to contribute to lowering the blood pressure, and a high content of these ions is considered very desirable.

Table 1 shows how the components in the pre-preparation formed in the fermentation step of the process according to the invention behave in the nanofiltration step. The composition is presented by way of example to illustrate the invention and it is produced by fermenting fat-free milk with a *Lactobacillus helveticus* strain. As clearly appears from the above description, also other products can be used as starting materials. Moreover, fermentation conditions, nanofiltration and other pretreatments and additional treatments, if any, contribute to the outcome, so the composition and the nanofiltration results of the end products may vary and differ from those presented herein.

TABLE 1

Behaviour in nanofiltration of whey components containing antihypertensive peptides.
Membrane: Nanomax 50; conditions: 40° C., 30 bar, volumatic concentration ratio C = 9, pH 4.6

| | Molecular weight D | Retention (%) |
|---|---|---|
| IPP | 361.4 | 100 |
| VPP | 347.4 | 100 |
| Lactic acid | 90.1 | 24 |
| Ca | 40.1 | 68 |
| Mg | 24.3 | 72 |
| K | 39.1 | 11 |
| Na | 23 | 10 |
| Cl | 35.5 | 9 |
| $PO_4$ | 95 | 47 |
| Urea | 60.1 | ~10 |
| Lactose | 342.3 | 63 |

The product concentrated for antihypertensive peptides and obtained by the process of the invention can be used as such as an antihypertensive agent. The product can also be dried and used in the form of a powder or a lyophilized preparation. In accordance with the present invention, the product is advantageously used in the manufacture of functional foods or other products, however.

In the present document, the term food is used in a broad sense covering all edible products which can be in solid, gelled or liquid form, and covering both ready-to-eat products and products to which the product of the invention is added in connection with consumption, as an additive or to be a constituent component of the product. For instance, foods can be products of dairy industry, meat processing industry, food processing industry, beverage industry, baking industry and confectionery industry. Typical products include milk products, such as yogurt, curdled milk, curd cheese, sour milk, buttermilk and other fermented milk beverages, unripened cheeses and ripened cheeses, snack fillings, etc. Beverages, such as whey beverages, fruit beverages and beers, constitute another important group.

The product obtained according to the invention is used in an amount sufficient to provide the desired, antihypertensive effect. The amount to be used depends significantly on the concentration degree of the whey, being e.g. 0.1 to 30%, preferably 5 to 15%, calculated from the weight of the end product.

Because the process of the invention, and in particular its nanofiltration step, provide a good framework for preparing a product of the desired type, it is also possible to reduce the contents of components having an adverse effect on taste or to remove said components completely and consequently to preserve or even improve the taste of the product.

The product containing antihypertensive peptides can be added to a food during the manufacturing process or to a ready-processed food. Said foods thus contain the above-described concentrated product containing antihypertensive peptides in addition to other ingredients that are conventional in such foods, and their taste and use completely correspond to those of the conventional products.

Thus, the two-step process according to the invention provides a product which has a considerably higher content of antihypertensive peptides than the products produced only by fermentation. Apart from the peptide content, the process also readily allows to adjust contents of salts and their mutual proportions to a desired level. In particular, it is possible to raise the content of desired divalent ions and to reduce the content of harmful monovalent ions. The process is simple and inexpensive, and it is well suited for large-scale production, and in this respect it differs from the prior art processes.

Moreover, it should be noted that the protein fraction obtained from the separation of casein or total protein can be used correspondingly in the manufacture of antihypertensive products, such as the above-described milk products or sausages, for instance. The process is thus highly economical on the whole.

In the following, the invention will be described in greater detail by means of examples. These examples are only intended to illustrate the invention, not to restrict its scope in any way.

REFERENCE EXAMPLE 1

Antihypertensive Effect of the Product of the Invention

ACE inhibitory activity was determined for the peptides IPP and VPP and for a known ACE inhibitor, lisinopril, on the basis of the so-called inhibitor constant (Holmquist B., Bunning P., Riordan J. F., A continuous spectrophotometric assay for angiotensin converting enzyme, *Analytical Biochemistry* 95 (1979) 540–548). The smaller the number, the more effective the ACE inhibitor. The results were as follows: IPP 4.4×10$^{-6}$, VPP 1.8×10$^{-5}$ and lisinopril 7.5×10$^{-9}$. IPP and VPP were thus found to have clear ACE inhibitory activity.

The antihypertensive effect of the product according to the invention was studied by giving, since birth, the sour milk product of the invention described in Example 5 to spontaneously hypertensive SHR rats. The controls consisted of three corresponding groups of rats that were given water, milk and commercially available sour milk, respectively. As reference was used a corresponding rat group that was given the Japanese Calpis sour milk product (by Calpis Food Industry Company Ltd.). The blood pressure of all rats was measured at one-week intervals for 13 weeks. The results are presented in FIG. 1 as the rise in the systolic pressure as a function of time. It appears clearly from the results that the product according to the invention is capable of preventing considerably elevation of blood pressure both as compared with the control groups and the reference group.

REFERENCE EXAMPLE 2

Antihypertensive Effect of the Product of the Invention

The antihypertensive effect of the product of the invention has also been studied on human beings. In a preliminary test, the test group consisted of 12 randomly selected persons who daily ingested 1.5 dl of the product of the invention described in Example 5 and the control group consisted of 11 randomly selected persons who ingested an equal amount of commercially available fat-free sour milk. Blood pressure was measured at one-week intervals for 8 weeks. The blood pressure of eight persons in the test group was clearly reduced: the systolic pressure for about 13% on the average and the diastolic pressure for about 12% on the average, one person was observed to have a minor, less than 5%, reduction in blood pressure, and three persons were observed to have no changes. In the control group, two persons were observed to have a clear reduction in blood pressure, whereas seven persons were observed to have no changes. The results of two persons were rejected. The results of this preliminary test thus show clearly that the product of the invention is capable of preventing considerably elevation of blood pressure in human beings.

EXAMPLE 1

Preparation of a Product Containing Antihypertensive Peptides

The strain *Lactobacillus helveticus* LBK 16-H was cultivated in MRS broth at a temperature of 37° C. for 24 hours and inoculated in reconstituted milk (10%) for producing an inoculum. After two cultivation rounds the inoculum (15%) was inoculated in a fermentor medium which was 9 to 10% milk made from fat-free milk powder milk and which was sterilized at 100° C. for 10 min. Fermentation was performed at 37° C. for 22 to 24 hours, by mixing strongly all the time. The product can be dried and pulverized or transferred as such to the nanofiltration treatment.

The pH of the fermented sour milk obtained in the above-described manner was raised to about 4.6 with KOH and the casein was removed with an inclined screen. Residual casein dust was removed by centrifugal clarifying. GLL Conc. lactase (Biocon Ltd., Japan) was added to the whey and it was allowed to hydrolyse at 5° C. for 24 hours for degrading the lactose into monosaccharides. The whey pretreated in this manner was nanofiltrated through a Nanomax-50 membrane (Millipore).

Filtration was performed at 40° C. in a pressure of 30 bar. The whey as filtered to a volumetric concentration ratio of 9. The compositions of the obtained concentrate and the dried powder produced therefrom are presented in Table 2.

TABLE 2

Compositions of a concentrate and a dried powder containing antihypertensive peptides

| | Peptide concentrate | Dried powder |
|---|---|---|
| Dry matter (%) | 30.0 | 94.5 |
| Ash (%) | 3.69 | 13.3 |
| Na (mg/kg) | 130 | 470 |
| K (mg/kg) | 1600 | 5600 |
| Ca (mg/kg) | 10000 | 36000 |
| Mg (mg/kg) | 1700 | 6300 |
| Cl (mg/kg) | 550 | 2000 |
| P (mg/kg) | 6700 | 24500 |
| IPP (mg/L) | 510 | 2500 |
| VPP (mg/L) | 540 | 2700 |

The removed casein was neutralized to caseinate and dried:

EXAMPLE 2

Preparation of a Product Containing Antihypertensive Peptides

The fermentation described in Example 1 was repeated by using (a) fat-containing milk and (b) butter milk in place of the fat-free milk.

The pH of the product of Example 2(b) was raised to about 4.5 and the casein was removed with a curd separator. Lactase was added to the whey and dust was removed with a bactofuge. The whey was then nanofiltrated through an NF membrane (Desal-5, Desal Inc.), evaporated and dried. The composition of the obtained nanofiltration concentrate was very similar to that presented in Table 2.

The removed casein comprises large amounts of whey whose anti-hypertensive peptide content equals to that of fermented sour milk. The casein was used as such in curd cheese, to which antihypertensive peptides were introduced in this manner.

EXAMPLE 3

Preparation of a Product Containing Antihypertensive Peptides

The strain *Lactobacillus helveticus* LBK 16-H was cultivated in MRS broth at 37° C. for 24 hours for producing an inoculum as described in Example 1. The inoculum was inoculated into a fermentor medium which consisted of an aqueous solution of casein precipitated with acid (2.8%) and glucose (2.5%). The casein was dissolved by raising pH to 6.7 with 10% KOH. The cultivation was carried out at 37° C. for 24 hours. In the product, it was possible to produce antihypertensive peptides (VPP, IPP) in amounts corresponding to those produced when fermenting milk, but it was easier to separate the peptides from the casein solution than from milk.

The pH of the fermentation broth was raised to 4.6 with KOH, at a temperature of 37° C., whereby the casein precipitated. The casein was separated with a curd separator and the obtained whey was recovered. The whey contains peptides, lactic acid and salts but no lactose. The major part of the lactic acid and monovalent salts and residual glucose of the whey can be removed by nanofiltration. The nanofiltration retentate can be evaporated to a concentrate or dried to powder, whereby a well concentrated and long preservable preparation containing antihypertensive peptides is obtained.

EXAMPLE 4

Preparation of a Product Containing Antihypertensive Peptides

Fermentation was repeated by using (a) a mixture of several strains, i.e. *L. helveticus* LB161, *L. helveticus* LBK-16H and *L. helveticus* LB230, (b) a mixture of the strains *L. helveticus* LBK-16H and *L. rhamnosus* LC705, and (c) a mixture of the strains *L. helveticus* LBK-16H and *Streptococcus thermophilus* T101. All these strains are available from the microorganism collection of Valio Oy.

The cultivation medium used was 9% milk that was sterilized at 100° C. for 15 min. For producing inocula, the *L. helveticus* strains and *L. rhamnosus* LC705 were cultivated in MRS broth for 24 hours, at 37° C., from which 1% inoculum was transferred into milk. *Str. thermophilus* T101 was cultivated in LM17 broth for 18 h, at 37° C., wherefrom an inoculum was transferred into milk.

The first cultivation was carried out by cultivating all strains separately in milk, incubation at 37° C. for 24 hours. For the second cultivation, 1% of the strains in each mixture was pipetted into milk, whereafter co-cultivation was continued for 24 hours, at 37° C. For the third cultivation, 5 to 10% of the previously obtained co-cultivation was pipetted into milk and incubated at 37° C. for 24 hours.

The amounts of VPP and IPP produced by the *L. heiveticus* LBK-16H strain and the different microbe mixtures and the concentration of some of the bacteria are presented in Table 3. No mutual differences were observed between the mixtures or the LBK-16H strain solely, but the other strains did not interfere with proteolysis either.

TABLE 3

IPP and VPP amounts produced by microbe mixtures

| Microbe (mixture) | VPP, mg/l | IPP, mg/l | Concentration cfu/ml |
| --- | --- | --- | --- |
| L161 + LBK-16 H + LB230, 5% | 13–14 | 6–7 | |
| L161 + LBK-16 H + LB230, 10% | 13–14 | 6–7 | |
| LBK16H + LC705, 5% | 13–14 | 6–7 | |
| LBK16H + LC705, 10% | 13–14 | 6–7 | |
| LBK16H + Str.T101 10% | 13–15 | 6–8 | $1 \times 10^8$ |
| LBK16H (solely) | 13–15 | 6–8 | $7 \times 10^7$ |

EXAMPLE 5

Preparation of a Fermented Milk Product

Sour milk containing antihypertensive peptides was prepared by adding 3.5% of the peptide concentrate obtained as in Example 3 to commercially available sour milk. The composition of the obtained product is presented in Table 4, which also shows the composition of the commercially available sour milk product, AB sour milk, by Valio Oy, for the sake of comparison.

TABLE 4

Composition of the product according to the invention and that of a commercially available fermented milk product

| | AB sour milk | Biopep-product of the invention |
| --- | --- | --- |
| Dry matter (%) | 9.0 | 9.8 |
| Na (mg/kg) | 390 | 380 |
| K (mg/kg) | 1700 | 1700 |
| Ca (mg/kg) | 1200 | 1510 |
| Mg (mg/kg) | 114 | 170 |
| Cl (mg/kg) | 1000 | 980 |
| VPP (mg/l) | 0 | 19 |
| IPP (mg/l) | 0 | 18 |

What is claimed is:

1. A process for preparing a product containing at least one antihypertensive tripeptide comprising the steps of:
   (a) fermenting a casein-containing starting material with a lactic acid bacterium to obtain a tripeptide-containing fermentation product, wherein said lactic acid bacterium is capable of producing at least one antihypertensive tripeptide;
   (b) filtering said tripeptide-containing fermentation product by nanofiltration; and
   (c) recovering a retentate of said nanofiltration to obtain the product containing at least one antihypertensive tripeptide.

2. The process as claimed in claim 1, wherein the starting material is casein.

3. The process as claimed in claim 1, wherein the starting material is milk or a milk-based product.

4. The process as claimed in claim 1, wherein a mixture of lactic acid bacteria and other microbes is used in the fermentation.

5. The process as claimed in claim 1, wherein the microorganism *Lactobacillus helveticus* is used in the fermentation.

6. The process as claimed in claim 5, wherein the microorganism is the strain *Lactobacillus helveticus* LBK-16H.

7. The process as claimed in claim 1, additionally comprising a step of removing casein from the fermentation product prior to nanofiltration.

8. The process as claimed in claim 1, additionally comprising a step of removing all milk proteins from the fermentation product prior to nanofiltration.

9. The process as claimed in claim 1, additionally comprising a step of removing lactose from the fermentation product prior to nanofiltration.

10. Product containing at least one antihypertensive tripeptide which is prepared by a process comprising the steps of:
    (a) fermenting a casein-containing starting material with a lactic acid bacterium to obtain a tripeptide-containing fermentation product, wherein said lactic acid bacterium is capable of producing at least one antihypertensive tripeptide;
    (b) removing at least some casein from said tripeptide-containing fermentation product prior to nanofiltration:
    (c) filtering said tripeptide-containing fermentation product by nanofiltration; and
    (d) recovering a retentate of said nanofiltration to obtain the product containing at least one antihypertensive tripeptide.

11. The product as claimed in claim 10, wherein said product contains a mixture of peptides hydrolyzed by proteolysis.

12. The product as claimed in claim 10, wherein said product contains di- and tripeptides.

13. The product as claimed in claim 10, wherein said product is comprised of at least one tripeptide selected from the group consisting of Ile-Pro-Pro and Val-Pro-Pro.

14. The product as claimed in claim 10, wherein said product has a high content of divalent cations.

15. The product as claimed in claim 10, wherein said product has a low content of monovalent cations.

16. The product as claimed in claim 10, wherein said product has a dry matter content of about 20 to 60%.

17. The product as claimed in claim 10, wherein said product is dried to powder and having a dry matter content exceeding 90%.

18. A method of using the product as claimed in claim 10, comprising orally ingesting said product as an antihypertensive agent.

19. A method of using the product as claimed in claim 10, comprising manufacturing an edible substance from said product.

20. The method as claimed in claim 19, wherein the edible substance is selected from the group consisting of a dairy product, a beverage, a processed food product, a processed meat product, a baked product and a confectionary product.

21. Edible product containing the product as claimed in claim 10.

22. The edible product as claimed in claim 21, wherein said product is a fermented milk product.

23. The edible product as claimed in claim 21, wherein said product is a beverage.

24. The edible product as claimed in claim 23, wherein said beverage is selected from the group consisting of a whey beverage, a fruit beverage and a beer.

\* \* \* \* \*